United States Patent
Bencivenga et al.

(10) Patent No.: US 11,267,774 B2
(45) Date of Patent: Mar. 8, 2022

(54) SYNTHETIC CANNABIDIOL COMPOSITIONS AND METHODS OF MAKING THE SAME

(71) Applicant: PureForm Global, Inc., Los Angeles, CA (US)

(72) Inventors: Marc Bencivenga, Los Angeles, CA (US); Matthew Forster, Novi, MI (US); Paul Herrinton, Novi, MI (US); Paul Jass, Franklin, WI (US); Surendra Singh, Shrewsbury, MA (US); Todd Zahn, Novi, MI (US)

(73) Assignee: PureForm Global, Inc., Los Angeles, CA (US)

( * ) Notice: Subject to any disclaimer, the term of this patent is extended or adjusted under 35 U.S.C. 154(b) by 0 days.

(21) Appl. No.: 16/805,278

(22) Filed: Feb. 28, 2020

(65) Prior Publication Data

US 2020/0199056 A1 Jun. 25, 2020

Related U.S. Application Data

(63) Continuation of application No. PCT/CN2018/049248, filed on Aug. 31, 2018.

(60) Provisional application No. 62/553,739, filed on Sep. 1, 2017.

(51) Int. Cl.
| | |
|---|---|
| *C07C 37/14* | (2006.01) |
| *C07C 39/23* | (2006.01) |
| *C07C 37/68* | (2006.01) |
| *C07C 37/72* | (2006.01) |
| *C07C 37/74* | (2006.01) |

(52) U.S. Cl.
CPC .............. *C07C 37/14* (2013.01); *C07C 37/68* (2013.01); *C07C 37/685* (2013.01); *C07C 37/72* (2013.01); *B01J 2531/26* (2013.01); *B01J 2531/35* (2013.01); *C07C 37/74* (2013.01); *C07C 39/23* (2013.01)

(58) Field of Classification Search
CPC combination set(s) only.
See application file for complete search history.

(56) References Cited

U.S. PATENT DOCUMENTS

| 2007/0093665 A1* | 4/2007 | Burdick | .................. C07C 35/16 |
| | | | 549/390 |
| 2015/0342902 A1* | 12/2015 | Vangara | .................. A61K 47/44 |
| | | | 514/729 |

FOREIGN PATENT DOCUMENTS

| WO | WO 2004/092101 | 10/2004 |
| WO | WO 2016/064987 | 4/2016 |

OTHER PUBLICATIONS

Kinney, W. A. et al. Supporting information for "Discovery of KLS-13019, a Cannabidiol-Derived Neuroprotective Agent, with Improved Potency, Safety, and Permeability"ACS Med. Chem. Lett. 2016, 7, 424-428; pp. 1-102 (Year: 2016).*

Kinney et al., "Discovery of KLS-13019, a cannabidiol-derived neuroprotective agent, with improved potency, safety, and permeability," *ACS Med. Chem. Lett.*, 7(4):424-428, and Supporting Information, Feb. 10, 2016.

Baek et al., "Boron trifluoride etherate on alimina—A modified lewis acid reagent. An improved synthesis of cannabidiol," *Tetrahedron Letters*, 26(8): 1083-1086, Jan. 1985.

International Search Report and Written Opinion issued for International Application No. PCT/US2018/049248 dated Dec. 17, 2018.

* cited by examiner

*Primary Examiner* — Medhanit W Bahta
(74) *Attorney, Agent, or Firm* — Klarquist Sparkman, LLP

(57) ABSTRACT

Disclosed herein are embodiments of a method for making cannabidiol. Also disclosed herein are embodiments of a composition comprising cannabidiol and one or more GRAS components. The method and composition embodiments described herein address the drawbacks associated with conventional methods for making and/or isolating cannabidiol.

20 Claims, No Drawings

SYNTHETIC CANNABIDIOL COMPOSITIONS AND METHODS OF MAKING THE SAME

CROSS REFERENCE TO RELATED APPLICATION

This application is a continuation of International Application No. PCT/US2018/049248, filed on Aug. 31, 2018, which claims the benefit of the earlier filing date of U.S. Provisional Patent Application No. 62/553,739, filed on Sep. 1, 2017; each of these prior applications is incorporated herein by reference in its entirety.

FIELD

Disclosed herein are embodiments of synthetic cannabidiol formulations and methods of making the same.

BACKGROUND

Cannabidiol is a cannabinoid that exhibits therapeutic properties and medical benefits, as well as cell- and tissue-protective properties, lending to its use in pharmaceuticals, cosmetics, and other areas. Cannabidiol has been shown effective in controlling seizures, managing pain, treating inflammation, and nourishing/protecting sensitive skin. Typically, cannabidiol does not exhibit the psychoactivity exhibited by tetrahydrocannabinol.

As cannabidiol exhibits utility in a variety of different applications, it is desirable to produce large quantities of this compound. Conventional methods for producing cannabidiol include isolating it from natural sources, such as agricultural hemp, or cannabis plants. These methods, however, often result in the concomitant presence of undesirable impurities, such as heavy metals and toxins absorbed by plants from soil. Cannabidiol also can be produced synthetically; however, current synthetic methods utilize reagents and/or purification components that introduce undesirable impurities that inhibit the ability to sell the cannabidiol under food/drug regulations. There exists a need in the art for a method for synthetically making cannabidiol that produces a substantially pure product, free of harmful and/or undesired impurities.

SUMMARY

Disclosed herein are embodiments of a method for making substantially pure cannabidiol. In some embodiments, the method can comprise forming crude cannabidiol and performing one or more additional steps, such as an aqueous alkaline wash procedure, or a complexation procedure, or a crystallization procedure, or any combination of such procedures. Also disclosed herein are embodiments of a complex comprising cannabidiol, such as an insoluble complex comprising cannabidiol and an amine compound, such as DABCO, caffeine (or 1,3,7-trimethyl-3,7-dihydro-1H-purine-2,6-dione), nicotinamide, isonicotinamide, 1,10-phenanthroline. Also disclosed herein are embodiments of a composition, comprising cannabidiol and a terpene-containing component. In some embodiments, the terpene-containing component can be a GRAS component.

The foregoing and other objects, features, and advantages of the present disclosure will become more apparent from the following detailed description, which proceeds with reference to the accompanying figures.

DETAILED DESCRIPTION

I. Overview of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods as understood by those of ordinary skill in the art. When directly and explicitly distinguishing embodiments from discussed prior art, the embodiment numbers are not approximates unless the word "about" is recited. Furthermore, not all alternatives recited herein are equivalents.

Compound embodiments disclosed herein may contain one or more asymmetric elements such as stereogenic centers, stereogenic axes and the like, for example, asymmetric carbon atoms, so that the chemical conjugates can exist in different stereoisomeric forms. These compound embodiments can be, for example, racemates or optically active forms. For compound embodiments with two or more asymmetric elements, these compound embodiments can additionally be mixtures of diastereomers. For compound embodiments having asymmetric centers, all optical isomers in pure form and mixtures thereof are encompassed by corresponding generic formulas unless context clearly indicates otherwise or an express statement excluding an isomer is provided. In these situations, the single enantiomers, i.e., optically active forms can be obtained by method known to a person of ordinary skill in the art, such as asymmetric synthesis, synthesis from optically pure precursors, or by resolution of the racemates. Resolution of the racemates can also be accomplished, for example, by conventional methods, such as crystallization in the presence of a resolving agent, or chromatography, using, for example a chiral HPLC column. All isomeric forms are contemplated herein regardless of the methods used to obtain them.

All forms (for example solvates, optical isomers, enantiomeric forms, polymorphs, free compound and salts) of an active agent may be employed either alone or in combination.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (+/−) D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory To facilitate review of the various embodiments of the disclosure, the following explanations of specific terms and abbreviations are provided:

Amine Compound: As used herein, this term refers to an amine compound capable of forming a complex with cannabidiol. In particular disclosed embodiments, the amine compound can have a structure satisfying a formula $NR^aR^bR^c$, wherein each of $R^a$, $R^b$, and $R^c$ independently is selected from hydrogen, aliphatic, aryl, heteroaliphatic, heteroaryl, or any combination thereof. In some embodiments, $R^a$ and $R^b$ (and/or) $R^c$ can join together to form a heterocyclic ring with the nitrogen atom to which they are bound, wherein the heterocyclic ring can further comprise one or more heteroatoms. In yet additional embodiments, the amine compound can include compounds having at least one pyridine ring, including, but not limited to, nicotinamide, isonicotinamide, and 1,10-phenanthroline.

Cannabidiol Degradation Product: A product formed from the chemical and/or thermal degradation of cannabidiol. Exemplary such products include, but are not limited to, $\Delta^l$-tetrahydrocannabinol; $\Delta^l$-tetrahydrocannabinol; dimers or trimers of cannabidiol (wherein the dimer or trimer is formed by carbon bond formation between two olefins of two cannabidiol molecules or by carbon-oxygen bond formation between a hydroxyl group of a cannabidiol molecule and a carbon atom of another cannabidiol molecule); products formed by carbon-carbon bond formation between starting materials, such as an olivetol molecule and two or more menthadienol molecules; regioisomeric and/or steroisomeric byproducts; and oxidative degradants of any of the aforementioned products. Chemical degradation can result from exposure of cannabidiol to acidic environments capable of degrading cannabidiol (for example, environments having a pH of less than 4, such as 1 to 4, or 1 to 3, or 1 or 2). Thermal degradation can result from exposure of cannabidiol to temperatures that cause molecular rearrangements of cannabidiol or dimerization or trimerization of multiple cannabidiol molecules, such as temperatures ranging from 24° C. to 170° C., such as 25° C. 170° C., or 25° C. to 150° C.

Complex/Insoluble Complex: As used herein in describing the product produced by combining cannabidiol with an amine compound, a complex, such as an insoluble complex (for example, a complex that is not readily soluble in a solvent), can comprise a salt formed between cannabidiol and the amine compound, a co-crystal formed between cannabidiol and the amine compound, a solvate formed between cannabidiol and the amine compound, or other complexation form.

GRAS: An acronym for the phrase "Generally Recognized As Safe," which is used in the United States to describe a component present in composition, such as the embodiments described herein, wherein the component is generally recognized by the U.S. Food & Drug Administration under Sections 201(s) and 409 of the Federal Food, Dug, and Cosmetic Act (these sections are incorporated herein by reference) as being safe under the conditions of its intended use. In some embodiments of the disclosed compositions, the use of a component may be defined as GRAS either through scientific procedures or through experience based on common use in food (for example, substantial history of consumption for food use by a significant number of consumers), wherein general recognition of safety through scientific procedures requires the same quantity and quality of scientific evidence as is required to obtain approval of the substance as a food additive. General recognition of safety through scientific procedures is based upon the application of generally available and accepted scientific data, information, or methods, which ordinarily are published, as well as the application of scientific principles, and may be corroborated by the application of unpublished scientific data, information, or methods.

Hydrocarbon Compound: A compound that consists of carbon and hydrogen atoms.

Lewis Acid Catalyst: A compound or ionic species that is capable of accepting an electron pair from a donor compound and that exhibits catalytic activity and typically includes a metal selected from aluminum, boron, silicon, tin, titanium, zinc, zirconium, iron, or copper. Exemplary Lewis Acid catalysts include, but are not limited to, $ZnCl_2$, $BF_3$, $SnCl_4$, $AlCl_3$, $Zn(OTf)_2$, $Sc(OTf)_3$, and $Cu(OTf)_2$.

Pharmaceutically Acceptable Excipient: A substance, other than the cannabidiol (or composition thereof) described herein or an active ingredient, that is included in a formulation of the active ingredient. An excipient may be incorporated within particles of a pharmaceutical formulation, or it may be physically mixed with particles of a pharmaceutical formulation. An excipient also can be in the form of a solution, suspension, emulsion, or the like. An excipient can be used, for example, to dilute an active agent and/or to modify properties of a pharmaceutical formulation. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients also can be starches and modified starches, cellulose and cellulose derivatives, saccharides and their derivatives such as disaccharides, polysaccharides and sugar alcohols, protein, synthetic polymers, crosslinked polymers, antioxidants, amino acids, peptides, or preservatives.

Substantially Pure/Substantially Purified: As used herein to describe the cannabidiol, these terms mean that the cannabidiol comprises less than 50% of an impurity (or mixture of impurities), such as less than 25%, or less than 15%, or less than 10%, or less than 5%, or less than 1%. In such embodiments, the recited percent values represent area percent, as determined by using chromatography (particularly gas chromatograph) and thus the area of the peak corresponding to an impurity can be directly related to the amount of the impurity present. Area percent of an impurity peak can be calculated with the following equation: Area=½ base×height. The amount of each impurity can then be determined by adding together the peak areas to get the total area of the peaks, and then dividing each area by the total area and multiplying by 100. In particular disclosed embodiments, the cannabidiol can still be substantially pure if it includes trace amounts of impurities, but such impurities are GRAS components or components meeting foreign food and/or drug safety regulations.

Terpene: A volatile hydrocarbon compound comprises at least one site of unsaturation typically found in natural sources, such as essential oils of plants and some insects. Terpenes typically comprise at least two isoprene (or $C_5H_8$) units.

Terpene-Containing Component: A component that can comprise one or more terpenes and that can, in some embodiments, itself be a terpene. In some embodiments, a terpene-containing component can further comprise a terpenoid. In an independent embodiment, the terpene-containing component comprises GRAS terpenes, or GRAS terpenoids, or any combinations thereof.

Terpenoid: A terpene that further comprises one or more functional groups and/or atoms other than just carbon and hydrogen.

II. Methods

Disclosed herein are embodiments of a method for making cannabidiol and compositions thereof. In some embodiments, the method comprises a continuous or semi-continuous process wherein suitable starting materials (for example, (+)-menthadienol and olivetol) are mixed together in the presence of a Lewis Acid catalyst to form a first reaction mixture comprising cannabidiol. The method can involve heating the first reaction mixture at a suitable temperature to result in the first reaction mixture reaching a temperature of greater than 25° C. to 170° C., such as 100° C. to 150° C., or 110° C. to 140° C., or 120° C. to 130° C. In some embodiments, a ratio of olivetol:(+)-menthadienol used in the method can range from 0.5:1 to 5:1, such as 0.75:1 to 2:1, or 1.1:1 to 1.3:1, or 1.75:1. In some embodiments, the starting materials can be reacted using a solvent-based method wherein one or more of the starting materials are diluted in a diluting solvent and then mixed together. Suitable diluting solvents for such methods can include, but are not limited to, aliphatic solvents (for example, heptane [including any isomers thereof], hexanes, pentane [including any isomers thereof], cyclohexane, heptanes, hexane [including any isomers thereof], and the like, including any and all combinations thereof); aromatic solvents (for example, benzene, toluene, ethylbenzene, xylenes, and the like, including any and all combinations thereof); and halogenated solvents (for example, 1,2-dichloroethane, dichloromethane, 1,2-dichloroethene, 1,1-dichloroethane, 1,1-dichloroethene, chlorobenzene, and the like, including any and all combinations thereof). The method can further comprise exposing the first reaction mixture comprising cannabidiol to a terpene-containing component (for example, orange terpenes) to form a second reaction mixture. The terpene-containing component can be added to the first reaction mixture as a solution or it can be added neat. In some embodiments, the terpene-containing component can be added in an amount such that the ratio of terpene-containing component (in weight equivalents) to total reagents present in the first reaction mixture can range from 0.05:1 to 10:1, such as 0.5:1 to 5:1, or 0.8:1 to 1.2:1. The second reaction mixture can then be exposed to an essentially pH neutral aqueous solvent (for example, water or other water-containing solution).

The method can further comprise separating an aqueous phase formed upon exposure of the second reaction mixture to the aqueous solvent from an organic phase. The organic phase comprises a crude product mixture comprising cannabidiol and the terpene-containing component. The crude product mixture is then exposed to an aqueous alkaline wash procedure wherein it is washed with an aqueous alkaline solution that removes unwanted impurities from the crude product mixture, such as any non-GRAS impurities, to provide a cannabidiol/terpene mixture. Suitable alkaline solutions can comprise water and an alkaline component, such as sodium hydroxide, potassium hydroxide, lithium hydroxide, sodium carbonate, potassium carbonate, lithium carbonate, sodium bicarbonate, potassium bicarbonate, and any combinations thereof. In some embodiments, the method can further comprise decolorizing the cannabidiol/terpene mixture using a filtration step, such as a silica gel filtration step.

In some embodiments, the cannabidiol is isolated from the terpene-containing component by using a complexation procedure, which includes forming an insoluble complex (for example, a salt, co-crystal, solvate, or other complexation form) with an amine compound, such as 1,4-diazabicyclo[2.2.2]octane (or "DABCO"), 1,3,7-trimethyl-3,7-dihydro-1H-purine-2,6-dione (also known as caffeine), nicotinamide, isonicotinamide, 1,10-phenanthroline. In some embodiments, the molar equivalent ration of amine:cannabidiol can range from 0.25:1 to 5:1, such as 0.5:1 to 2:1, or 1:1 to 1.5:1 In some embodiments, trace amounts of the terpene-containing component can be present in subsequent steps following the filtration step discussed above. The complexation procedure can further comprise isolating the resulting insoluble complex by filtration or centrifugation.

In yet additional embodiments, the method can further comprise a crystallization procedure. In some embodiments, the crystallization procedure can comprise converting the resulting complex back to the free cannabidiol species by dissolving the complex in a solvent mixture. In some embodiments, the solvent mixture can comprise a glycol (for example, propylene glycol) and dilute aqueous acid (for example, hydrochloric acid, sulfuric acid, phosphoric acid, or any combination thereof). In some embodiments, the ratio of solvent:acid can be 5:1 or greater (for example, 5.5:1 or 6:1). In some embodiments, the solvent mixture is combined with the complex at ambient temperature.

In some embodiments, the solution resulting from dissolving the complex in the solvent mixture can be clarified using a filtration step, but such a filtration step is not required. If a filtration step is used, crystallization can be performed subsequent to the filtration step. In embodiments where a filtration step is not used, crystallization can be performed after redissolving the cannabidiol in the solvent mixture. In some embodiments, crystallization includes mixing the filtered solution or the solution obtained from redissolving the cannabidiol in the solvent mixture with water to thereby induce crystallization. In yet additional embodiments, the crystallization procedure can further comprise a seeding step whereby one or more seed crystals are added. In some embodiments utilizing a seeding step, the seed crystals can be added in an amount ranging from 0.1 wt % to 2 wt % based on the weight of cannabidiol present in the composition to which the seed crystals are added. The resulting solid can be isolated using a filtration or centrifugation step and can then be washed with water. Any number of washing steps can be used, such as one to ten washing steps, or one to five, or two to four washing steps.

In some embodiments, the isolated solids are then combined with a dilute aqueous alcohol solution to form a slurry. In some embodiments, the dilute aqueous alcohol solution can comprise aqueous ethanol, such as 5-25% aqueous ethanol. The slurry is then filtered to isolate the resulting solids, which are then washed with water and dried to provide the substantially purified cannabidiol. In some embodiments, the slurry-formation step can be replaced by using more washing steps with the water.

A representative method is summarized below in Scheme 1.

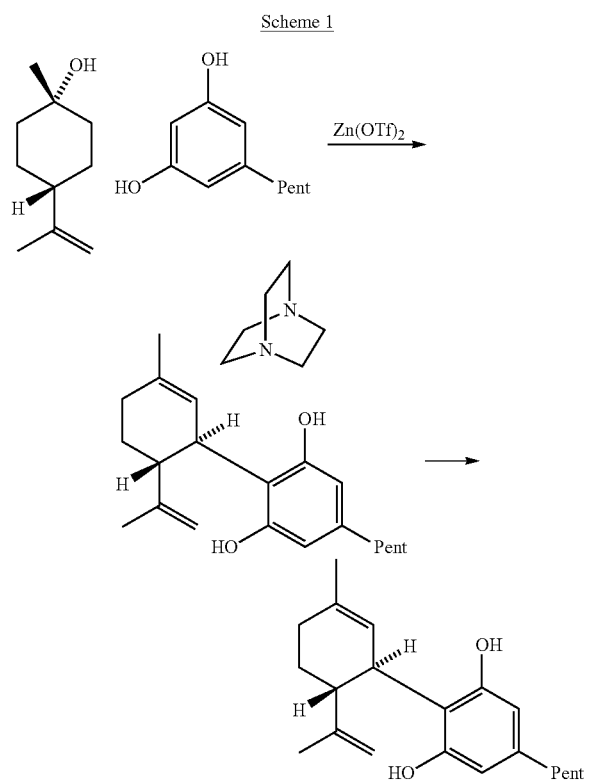

With reference to Scheme 1, some representative embodiments involve combining olivetol and Zn(OTf)$_2$ and then adding methandienol. In yet other embodiments, methandienol and olivetol can first be combined and then Zn(OTf)$_2$ is added. In either of these embodiments, the methandienol and olivetol can be used neat or can first be diluted with a suitable solvent as discussed herein. In some embodiments, the olivetol can be heated so as to have a reaction temperature of 120° C. to 125° C. and then Zn(OTf)$_2$ is added, followed by methandienol. The resulting reaction mixture can then be heated (or the temperature can be maintained) such that the reaction temperature ranges from 120° C. to 125° C. A terpene component can be added while cooling the reaction mixture, followed by water addition. The reaction temperature can then be adjusted to 20° C. to 25° C. The reaction mixture can then be allowed to settle so as to allow the organic and aqueous layers to separate. After removing the aqueous layer, the organic phase can be exposed to an alkaline wash using 10% NaOH. The resulting aqueous layer can be removed and then the resulting isolated organic solution can be filtered through silica and washed with an additional amount of the terpene component. An amine can be added to facilitate complexation and formation of a solid complex formed between the CBD and the amine. This complex can be exposed to one or more washing steps using the terpene component, ether, or both, followed by a drying step. The dried complex can then be combined with a solvent, such as propylene glycol, and acidified with HCl, thereby providing the uncomplexed CBD. This product can be crystallized using a seeding process, followed by water addition and filtering. One or more washing steps can be used, including washing with water, ethanol, or a combination thereof. The resulting purified CBD is then isolated in high purity.

The method described above provides a cost effective and efficient way to prepare cannabidiol that is substantially pure. Additionally, even if the above method embodiments result in cannabidiol having some level of impurity present, the impurity is such that any present impurities are compliant with the requirements for such components to be characterized as GRAS in the United States. The cannabidiol and compositions thereof disclosed herein also are suitable for uses outside the United States as any trace impurities present with the cannabidiol also are recognized as safe for use in food, pharmaceuticals, and cosmetics in foreign countries. As such, the cannabidiol produced by the method embodiments disclosed herein, including the compositions described herein, can be used in the medical, cosmetic, and food industries without expensive purification steps and/or further purification treatments. In some embodiments, the cannabidiol or composition embodiments disclosed herein can be used as a therapeutic or they can be combined with other therapeutic agents and/or pharmaceutically acceptable excipients.

III. Compositions

Disclosed herein are composition embodiments comprising cannabidiol and one or more "generally recognized as safe" (or GRAS) components. In some embodiments, the GRAS components also are components that comply with foreign food and/or drug safety regulations (for example, food additive regulations), such as the European Food Safety Authority. In an independent embodiment, the composition can consist essentially of cannabidiol and one or more GRAS components. In such composition embodiments, "consist essentially of" means that the composition is free of any components that do not fall within the scope of GRAS, such as some heavy metals, and/or components that have a deleterious effect on human health. In another independent embodiment, the composition can consist of cannabidiol and one or more GRAS components.

Cannabidiol has a structure as illustrated in Structure 1 below and typically has the stereochemistry illustrated in Structure 2 below:

Structure 1

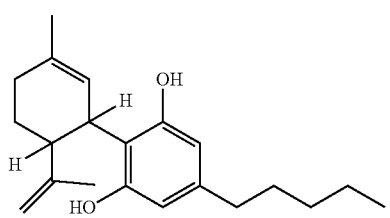

-continued

Structure 2

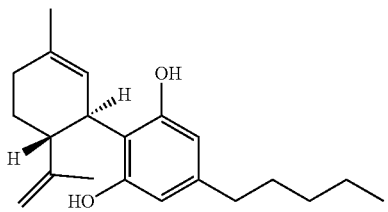

In some embodiments, the one or more GRAS components can be selected from a terpene-containing component (for example, orange terpenes; limonene [which can include D-limonene, L-limonene, or a combination thereof] and other terpenes or terpenoids present in orange terpenes; valencene, aristolochene, or any combination thereof); an oil (for example, orange oil, cedarwood oil, grapefruit oil, or any combination thereof); a GRAS solvent (for example, a propylene glycol, such as 1,2-propanediol or 1,3-propanediol; water; glycerol; alcohol, such as ethanol, isopropanol, or butanol; or any combinations thereof); or any combination of such components. In some embodiments, the composition can comprise a derivative or byproduct produced by thermal and/or chemical degradation of a GRAS terpene-containing component. The derivative or byproduct also can be classified as GRAS. In some embodiments, the amount of the GRAS component present in the composition embodiments can range from greater than 0% to less than 50% of the total composition, such as 0.0001% to 25%, or 0.001% to 15%, or 0.01% to 10%, or 0.1% to 5%, or 1% to 10%. In some embodiments, the amount of the GRAS component is less than 5% of the total composition and in yet additional embodiments can be less than 0.1% of the total composition. The amount of cannabidiol present in composition embodiments described herein can range from greater than 50 wt % to less than 100 wt % of the total composition, such as 75 wt % to 99.9999 wt %, or 85 wt % to 99.999 wt %, or 90 wt % to 99.99 wt %, or 95 wt % to 99.9 wt % or 95 wt % to 99 wt % of the total composition.

In particular disclosed embodiments, the composition comprises cannabidiol and orange terpenes that are obtained from a commercial source. Commercially supplied orange terpenes can include a mixture comprising a majority component (for example, greater than 50 wt % to 99 wt % of the total composition, such as 75 wt % to 99 wt %, or 85 wt % to 99 wt %, or 95 wt % to 99 wt % of the total composition) of D-limonene and a minor component (for example, greater than 0 to less than 50 wt % of the total composition, such as 1 wt % to 25 wt %, or 1 wt % to 15 wt %, or 1 wt % to 10 wt %, or 1 wt % to 5 wt %) that can comprise one or more terpenoids (for example, terpenoids formed from limonene), or any combination thereof. Exemplary minor components can include, but are not limited to, myrcene, valencene, linalool, octanal, decanal, ethyl butyrate, or other components described in Hognadottir and Rouseff, J. of Chromatography A, 998 (2003), 201-211, which is incorporated herein by reference.

In some embodiments, the composition can be free or substantially free of cannabidiol degradation products. Compositions free of cannabidiol degradation products typically have no traceable amounts of such products. Compositions essentially free of cannabidiol degradation products typically have less than 5% of such products, such as less than 4%, or less than 3%, or less than 2%, or less than 1%, or less than 0.5%.

In particular disclosed embodiments, the composition can be analyzed using a suitable characterization method to evaluate/determine whether a GRAS component is present in the composition, how much of the GRAS component is present in the composition, and/or to identify a GRAS component that is present in the composition. Suitable characterization methods include, but are not limited to, gas chromatography (or "GC"), nuclear magnetic resonance (or "NMR") spectroscopy, high-performance liquid chromatography (or "HPLC"), infrared (or "IR") spectroscopy, thin layer chromatography (or "TLC"), mass spectrometry (or "MS"), ultraviolet-visible (UV-vis) spectroscopy, melting point analysis, and any combination of such methods. In any of these embodiments, a cannabidiol reference that is free of any trace amounts of other compounds and that has been characterized using any of these methods can be used to determine if GRAS components are present. In some embodiments, characterization data for pure cannabidiol is publically available and can be used as a cannabidiol reference.

In particular disclosed embodiments, GC and/or HPLC can be used and in such embodiments, a GRAS component will elute from the column and can be identified as a peak on a resulting chromatogram. A person of ordinary skill in the art with the benefit of the present disclosure will recognize that carrier gas selection (or mobile phase selection for HPLC), flow rates, stationary compound selection, inlet type, sample size, column type, and/or column temperature can be controlled in order to observe a peak corresponding to a GRAS component that has a retention/elution time from a peak corresponding to cannabidiol.

In other embodiments, NMR spectroscopy can be used to determine the presence, amount, and/or identify of a GRAS component. Proton and/or carbon NMR analysis can be used, as can 2-dimensional NMR techniques, such as ROESY, NOESY, COSY, HSQC, and/or HMBC. In particular embodiments, if a composition embodiment comprising a GRAS component is analyzed using an NMR technique, such as proton or carbon NMR, one or more peaks that do not correspond to peaks associated with the structure of cannabidiol will be present.

If IR analysis is used, then the presence and/or identify of a GRAS component can be determined from the resulting spectrum, which will typically have a characteristic peak or fingerprint region associated with a functional group of the GRAS component. Solely by way of example, if ethanol is present in the composition, a peak corresponding to the —OH group of ethanol can be present in the spectrum.

In yet additional embodiments, if TLC analysis is used to analyze a composition embodiment, then a GRAS component could be detected as evidenced by a component having a retention time that differs from the cannabidiol. For example, if a terpene GRAS component is present in the composition, then it could be detected if it has a retention time different from that of the cannabidiol. However, if TLC analysis only produces one spot corresponding to the cannabidiol, it does not necessarily mean that no GRAS component is present as other GRAS components contemplated herein may not be detectable using TLC.

In yet additional embodiments, composition embodiments described herein can be analyzed using MS characterization techniques. If a GRAS component capable of being detected with MS is present in the composition, then its identity can be determined/confirmed using MS as this technique can produce a molecular ion peak that corresponds to the molecular weight of the heaviest ion of the GRAS component. In some embodiments, a particular fragmenting pattern can be observed using MS that also can be used to identify the GRAS component.

In some embodiments, the composition embodiments can be analyzed using UV-vis spectroscopy to determine the presence and/or amount of a GRAS component present in the composition. In such embodiments, the GRAS component can absorb light at a particular wavelength and therefore will produce a peak in the resulting absorbance spectrum. The concentration/amount of the GRAS component can be calculated from its corresponding absorbance peak using methods known to those of ordinary skill in the art with the benefit of the present disclosure, such as the Beer-Lambert law.

Additionally, melting point analysis can be used to determine whether a GRAS component is present. In some embodiments, if a cannabidiol specimen is analyzed and includes a GRAS component, it can have a large melting point range (for example, a difference of 3° C. to 10° C. between the temperature at which the specimen begins to melt to the temperature at which it is completely melted).

IV. Examples

Example 1A—Exemplary Reaction to Form Crude Cannabidiol from Neat Reactants

This example describes a representative method for making crude cannabidiol according to the method embodiments described herein. In this example, the method comprises the following steps:
- Charging a holding vessel with 50 g (328 mmol) of (+)-menthadienol, the contents of which can be rapidly transferred to another vessel;
- Charging the reaction vessel with 80±20 g (443±111 mmol) of olivetol and stir the contents at ambient temperature or heat the contents such that the internal temperature of the reaction vessel reaches a temperature ranging from greater than 25° C. to 170° C. In particular examples, the contents were heated until the internal temperature of the reaction vessel reached 150° C.;
- Charging the reaction vessel with 0.06 to 0.48 g (0.16 mmol to 1.31 mmol) of $Zn(OTf)_2$. In particular examples, the reaction vessel was charged with 0.38 g (1.05 mmol) $Zn(OTf)_2$;
- Rapidly charging the contents of the holding vessel (50 g (328 mmol) of (+)-menthadienol) to the reaction vessel containing olivetol and $Zn(OTf)_2$, over about 30 seconds to 2 minutes, preferably about 45 seconds;
- Immediately charging the reaction vessel with 10 to 160 g (7.3 mmol to 1.17 mol) of a hydrocarbon solvent (for example, heptane [including any isomers thereof], cyclohexane, heptanes, petroleum ether, pentane [including any isomers thereof], hexane [including any isomers thereof], or the like), or orange oil, or limonene, or any combination thereof. In particular examples, orange terpenes were used;
- Mixing the mixture for 0 to 600 seconds. In particular examples, the preferred time was 30 seconds;
- Transferring the crude mixture to a vessel that contains 10 to 300 g (0.55 mol to 16.6 mol) of water. In particular examples, 160 g (8.9 mol) of water was used; and
- Agitating and cooling the reaction mixture to 10 to 40° C. In particular examples, the temperature range was 20 to 30° C. The organic and aqueous phases were then separated and the aqueous phase was discarded.

Example 1B—Exemplary Reaction to Form Crude Cannabidiol with Solvent

This example describes embodiments of a representative solvent-based method for making crude cannabidiol according to the method embodiments described herein. In this example, three different solvent embodiments were used and are described below.

Example 1B.1: Toluene Solvent

A 22000 ml 4-neck round bottom flask equipped with heating mantle, thermocouple, mechanical stirring, condenser, and addition funnel was charged with olivetol (1046 g, 5.748 moles) and toluene (7500 ml) and the flask was swept with argon for 5 minutes.

The reaction was heated to 80° C. and zinc triflate (23.9 g, 0.0657 moles) was added all at once as a solid. To the addition funnel was charged a solution of p-menthadienol (500 g, 3.284 moles) in toluene (2500 ml).

The temperature was raised to 100° C. and the solution was added dropwise over approximately one hour. The reaction was sampled at 100% addition and 30 minutes after the addition was completed and run on HPLC Standard 1. The reaction was complete after 30 minutes.

1000 ml of $H_2O$ was added to the reaction to quench and the reaction was allowed to cool to room temperature. The quench was added carefully to avoid considerable boiling as it cooled down. The phases were separated and the organics were concentrated to a crude oil (1521 g).

Example 1B.2: Heptane Solvent

A 12000 ml 3-neck round bottom flask equipped with heating mantle, thermocouple, mechanical stirring, condenser, and addition funnel was charged with olivetol (518 g, 2.874 moles) and heptane (3750 ml). The flask was swept with argon for 5 minutes.

The reaction was heated to 80° C. and zinc triflate (3 g, 0.0082 moles) was added all at once as a solid.

The reaction temperature was raised to 93° C. To the addition funnel was charged a solution of p-menthadienol (250 g, 1.642 moles) in heptane (1250 ml). The reaction was sampled at 100% addition and 15 minutes after the addition was completed and run on HPLC Standard 1. The reaction was complete after 15 minutes. 1000 ml of $H_2O$ was added to the reaction to quench and the reaction was allowed to cool to room temperature.

Example 1B.3: 1,2-Dichloroethane Solvent

A 5000 ml 3-neck round bottom flask equipped with heating mantle, thermocouple, mechanical stirring, condenser, and addition funnel was charged with olivetol (207 g, 1.150 moles) and dichloroethane (1500 ml). The flask was swept with argon for 5 minutes.

The reaction was heated to 74° C. and zinc triflate (4.77 g, 0.0013 moles) was added all at once as a solid. The reaction temperature was raised to 78° C. (gentle reflux). The addition funnel was configured above the condenser. To the addition funnel was charged a solution of p-menthadienol (100 g, 0.657 moles) in dichloroethane (500 ml).

The reaction was sampled at 100% addition and again after 1 hour and 2 hours after the addition was completed and run on HPLC Standard 1. The reaction was complete after two hours. 1000 ml of $H_2O$ was added to the reaction to quench and the reaction was allowed to cool to room temperature. The phases were separated and the organics were concentrated to an orange oil (crude 1, 304.4 g).

Example 2—Exemplary Aqueous Alkaline Wash Procedure

This example describes embodiments of a representative method for performing an aqueous alkaline washing step according to the method embodiments described herein.

Example 2.1

In this embodiment, the product from Example 1A was washed by:
Charging a reaction vessel comprising the organic phase formed above with 10 to 320 g of a dilute aqueous alkaline solution. In particular examples, the organic phase was combined with 160 g of 10% sodium hydroxide solution;
Agitating the mixture for 5 to 15 minutes, allowing the organic and aqueous phases to separate, and discarding the aqueous phase; and
Filtering the organic solution to clarify. In particular examples, a silica gel filtration aid was used.

Example 2.2

In another example, the crude oil from Example 1B:1 above was subjected to the following steps:
The oil was dissolved in heptane (9000 ml) and washed with 5000 ml of 3M NaOH.
The phases were allowed to separate over 45 minutes and the resulting organics were washed 2×4000 ml $H_2O$.
The combined organics were dried over magnesium sulfate and filtered through a pad of celite. The organics were concentrated to a crude oil (513 g).

Example 2.3

In another example, the crude oil from Example 1B.2 above was subjected to the following steps:
1000 ml of $H_2O$ was added to the reaction to quench and the reaction was allowed to cool to room temperature. The organics were washed with 10% NaOH (2500 ml). The biphasic mixture turned a dark red color.
The phases were allowed to separate over 1 hour.
The organics were then washed with 2×2000 ml of $H_2O$. The organics were concentrated to a light orange oil (367 g).

Example 2.4

In yet another example, the oil from Example 1B.3 above was subjected to the following steps:
The oil was dissolved in heptane (1000 ml) and washed with 10% NaOH (1000 ml). The biphasic mixture turned a dark red color.
The organics were then washed with 2×1000 ml of $H_2O$. The organics were concentrated to a light orange oil (124.3 g).

Example 3—Exemplary Complexation Procedure

This example describes embodiments of a representative method for forming a cannabidiol complex according to method embodiments described herein.

Example 3.1

In this example, the product from Example 2.1 was exposed to a method comprising the following steps:
Adding 3.68 to 36.8 g (3.28 mmol to 328 mmol) of an amine compound to the clarified solution isolated from the aqueous alkaline wash above. In particular examples, DABCO was used as the amine compound and it was used in an amount of 12.9 g (115 mmol);
Agitating the mixture for 5 to 90 minutes. In particular examples, the mixture was agitated for 45 to 60 minutes;
Isolating the CBD•DABCO insoluble complex via filtration or centrifugation;
Washing the solids with 0.5 to 2 cake volumes of a hydrocarbon solvent (for example, heptane [including any isomers thereof], cyclohexane, heptanes, petroleum ether, pentane [including any isomers thereof], hexane [including any isomers thereof], or the like). In particular examples, petroleum ether was used to displace the mother liquor; and
Drying the CBD•DABCO complex at 20° C. to 60° C. (such as 45° C.) under vacuum.

Example 3.2

In this example, the product from Example 2.2 was exposed to a method comprising the following steps:
The oil was dissolved in 5 ml/g (2500 ml) of heptane and stirred at 55° C. for 5 minutes. DABCO was added all at once as a solid (160 g, 1.1 equivalents based on area by HPLC) to the oil. The solids quickly went into solution until a white solid precipitated from the solution.
The slurry was then stirred for 45 minutes at room temperature.
The solids were filtered, washed with heptane, and dried on the fritted funnel (757.1 Mass of any DABCO salt are approximate because they are not dried thoroughly.
The solids were charged to a flask and heptane was added (2000 ml). The slurry was stirred at 55° C. for five minutes and then for 45 minutes at room temperature. The DABCO solids were filtered and dried on the frit (647.3 g).

Example 3.3

In this example, the product from Example 2.3 was exposed to a method comprising the following steps:
The oil was dissolved in heptane (1000 ml) and charged to a round bottom flask. To the flask was charged DABCO all at once as a solid (113 g, 1.1 equivalents based on 79% area by HPLC).
The mixture was stirred in a 55° C. bath for 10 minutes and then allowed to stir for 30 minutes at room temperature. More heptane was added as needed (for stirring) after the DABCO salt of CBD began to crystallize to allow for stirring. While stirring in the hot water bath, the DABCO appeared to go into solution and then a solid crashed out. After stirring at room temperature, the solids were filtered and washed with heptane (147.5 g).

The solid was charged to a 5000 ml flask and 100 ml of heptane was added and the process of stirring hot (55° C. for 10 minutes) followed by room temperature (30 minutes) was repeated. The resulting light pink solid was filtered and washed with heptane (118.2 g). Mass of DABCO salts is approximate as they are not thoroughly dried. HPLC Standard 1 indicated that the solid was 95% by HPLC Standard 1.

Example 3.4

In this example, the product from Example 2.4 was exposed to a method comprising the following steps:
The oil was dissolved in heptane (500 ml) and charged to a round bottom flask. To the flask was charged DABCO all at once as a solid (32.4 g, 1.1 equivalents based on 66.9% area by HPLC),
The mixture was stirred in a 55° C. bath for 10 minutes and then allowed to stir for 30 minutes at room temperature. More heptane was added as needed after the DABCO salt of CBD began to crystallize to allow for stirring. While stirring in the hot water bath, the DABCO appeared to go into solution and then a solid crashed out. After stirring at room temperature, the solids were filtered and washed with heptane (147.5 g).
The solid was charged to a 2000 ml flask and 500 ml of heptane was added and the process of stirring hot (10 minutes) followed by room temperature (30 minutes) was repeated. The resulting light pink solid was filtered and washed with heptane (118.2 g). HPLC Standard 1 indicated that the solid was >99% pure.

Example 4—Exemplary Crystallization Procedure

This example describes a representative method for redissolving a cannabidiol complex to reform cannabidiol and crystallizing it.

Example 4.1

In this example, the method comprises the following steps:
Charging an appropriately sized vessel with 50 g (117 mmol) of the CBD•DABCO complex;
Charging the vessel with 100 to 800 g (1.3 mol to 10.5 mol) of propylene glycol to the vessel with the CBD•DABCO complex. In particular examples, 383 g (5.18 mol) of propylene glycol was used for the CBD•DABCO complex of Example 3.1;
Charging the vessel with 30 to 71.2 g (49 mmol to 117 mmol) of 2 N mineral acid. In particular examples, 57.4 g (95 mmol) of HCl was used;
Clarifying the solution by filtration;
Charging a vessel comprising the clarified solution with 25 to 125 g (1.39 mol to 6.9 mol) of water to the solution over 15 to 600 minutes. In particular examples, 74 g (4.1 mol) of water was used and it was charged to the vessel over a time period of 60 to 180 minutes; and
Agitating the slurry for 0.5 to 24 hours. In particular embodiments, the slurry was agitated for 2 to 4 hours.

Example 4.2

In this example, the CBD•DABCO complex from Example 3.2 was treated as follows:

The CBD•DABCO complex was slurried in 2500 ml of heptane and 3500 ml of 0.5 Pel HCl was added. The solids went into solution and the organic phase turned from pink to green. The organics were washed with water (2000 ml) and dried over magnesium sulfate. The resulting solution was concentrated to a yellow oil which was drained into trays where it crystallized (373.9 g). $^1$H NMR and HPLC (CBD method) confirmed purity and product.

Example 4.3

In this example, the CBD•DABCO complex from Example 3.3 was treated as follows:
To a 12000 mli round bottom flask was charged the CBD•DABCO complex and heptane (1250 ml). The flask was equipped with magnetic stirring and charged with 2500 ml of 0.5 ml HCl solution. The two phase mixture was stirred vigorously for 10 minutes. The solids went into solution and the color changed from pink to green. The phases were separated. The organics were washed with water (1000 ml). The organics were filtered through a pad of magnesium sulfate and the filtrate was concentrated to a very viscous oil (209.4 g). The oil was dropped into a tray containing a seed crystal. The oil crystallized overnight. The crystals were broken up and milled using a mortar and pestle. The resulting powdery white yellow solids were approximately 95% area by HPLC.

Example 4.4

In this example, the CBD•DABCO complex from Example 3.4 was treated as follows:
To a 2000 ml round bottom flask was charged the CBD•DABCO complex and heptane (300 ml). The flask was equipped with magnetic stirring and charged with 1000 ml of 0.5 ml HCl solution. The biphasic mixture was stirred vigorously for 10 minutes. The solids went into solution and the color changed from pink to green. The phases were separated. The organics were washed with water (100 ml). The organics were filtered through a pad of magnesium sulfate and the filtrate was concentrated to a very viscous oil (88 g). The oil was dropped into a tray containing a seed crystal. The oil crystallized overnight. The crystals were broken up and milled using a mortar and pestle. The resulting powdery white yellow solids were >99% by HPLC.

Example 5—Exemplary Isolation and Drying Modification to Crystallization Procedure This example describes a representative method for isolating and drying substantially pure cannabidiol. In this example, the method comprises the following steps:
Isolating the solids from the above complex break and crystallization process via filtration or centrifugation;
Washing the solids with 0.5 to 2 cake volumes of water;
Forming a slurry with the solids in 200 to 600 of 5 to 25% aqueous ethanol. In particular examples, 415 g of aqueous ethanol was used;
Filtering the solids and wash the cake with 0.5 to 2 cake volumes of water; and
Drying the resulting crystals at 25 to 55° C. under vacuum to constant weight.

Example 6—Characterization

The melting point of the complex formed between cannabidiol and DABCO was determined, in this example, to be 120° C.-122° C.

V. Overview of Several Embodiments

Disclosed herein are embodiments of a composition, comprising cannabidiol and a terpene-containing component. In some embodiments, the terpene-containing component is a GRAS component.

In any or all of the above embodiments, the terpene-containing component comprises orange terpenes, or valencene, or aristolochene, or limonene or any combination thereof.

In any or all of the above embodiments, the limonene is D-limonene.

In any or all of the above embodiments, the composition can further comprise one or more GRAS solvents. In some embodiments, the one or more GRAS solvents are propylene glycol, or water, or glycerol, or ethanol, or any combination thereof.

In any or all of the above embodiments, the cannabidiol is present in an amount ranging from greater than 50% to less than 100%.

In any or all of the above embodiments, the composition is free of cannabidiol degradation products.

In any or all of the above embodiments, the cannabidiol degradation products are formed by thermal and/or chemical degradation of cannabidiol. In some embodiments, the cannabidiol degradation products comprise $\Delta^1$-tetrahydrocannabinol; $\Delta^1$-tetrahydrocannabinol; dimers or trimers of cannabidiol; products formed by carbon-carbon bond formation between an olivetol molecule and two or more menthadienol molecules; regioisomeric products; steroisomeric byproducts; and oxidative degradation products.

Also disclosed herein are embodiments of a synthetic cannabidiol composition, comprising: cannabidiol; and D-limonene, provided that the composition does not include a non-GRAS component, a cannabinoid other than cannabidiol, $\Delta^1$-tetrahydrocannabinol; $\Delta^1$-tetrahydrocannabinol; dimers or trimers of cannabidiol; products formed by carbon-carbon bond formation between an olivetol molecule and two or more menthadienol molecules, or other cannabidiol degradation products.

Also disclosed herein are embodiments of a composition consisting of cannabidiol and one or more GRAS components.

Also disclosed herein are embodiments of a method, comprising combining (+)-menthadienol and olivetol with a Lewis Acid catalyst to form a first reaction mixture; exposing the first reaction mixture to a terpene-containing component to form a second reaction mixture; exposing the second reaction mixture to water to form an organic phase and an aqueous phase; and separating the organic phase from the aqueous phase. In some embodiments, the Lewis Acid catalyst is $Zn(OTf)_2$ or $Sc(OTf)_3$.

In any or all of the above embodiments, the terpene-containing component is orange oil, orange terpenes, limonene, or a combination thereof.

In any or all of the above embodiments, the (+)-menthadienol and olivetol are mixed together and then the Lewis Acid catalyst is added.

In any or all of the above embodiments, the olivetol and the Lewis Acid catalyst are mixed together and then the (+)-menthadienol and is added.

In any or all of the above embodiments, the olivetol, the (+)-menthadienol, or both are diluted with a solvent prior to combining the olivetol and the (+)-menthadienol.

In any or all of the above embodiments, the solvent is selected from an aliphatic solvent, an aromatic solvent, or a halogenated solvent.

In any or all of the above embodiments, the aliphatic solvent can be heptane, hexanes, pentane, cyclohexane, heptanes, hexane, or any and all combinations and/or isomers thereof.

In any or all of the above embodiments, the aromatic solvent can be benzene, toluene, ethylbenzene, xylenes, or any and all combinations thereof.

In any or all of the above embodiments, the halogenated solvent can be 1,2-dichloroethane, dichloromethane, 1,2-dichloroethene, 1,1-dichloroethane, 1,1-dichloroethene, chlorobenzene, or any and all combinations thereof.

In any or all of the above embodiments, the method can further comprise performing an aqueous alkaline wash procedure, or a complexation procedure, or a crystallization procedure, or any combination of such procedures. In some embodiments, the aqueous alkaline wash procedure comprises: exposing the organic phase to an aqueous alkaline solution; mixing the organic phase with the aqueous alkaline solution; and filtering the organic phase to provide a clarified solution.

In any or all of the above embodiments, the complexation procedure comprises mixing the organic phase or the clarified solution with an amine compound for a time sufficient to produce an insoluble complex; isolating the insoluble complex via filtration or centrifugation; and washing the insoluble complex with a solvent. In some embodiments, the amine compound is 1,4-diazabicyclo[2.2.2]octane, 1,3,7-trimethyl-3,7-dihydro-1H-purine-2,6-dione, nicotinamide, isonicotinamide, or 1,10-phenanthroline.

In any or all of the above embodiments, the insoluble complex comprises (i) cannabidiol and (ii) 1,4-diazabicyclo[2.2.2]octane, or 1,3,7-trimethyl-3,7-dihydro-1H-purine-2,6-dione, or nicotinamide, or isonicotinamide, or 1,10-phenanthroline.

In any or all of the above embodiments, the solvent is petroleum ether.

In any or all of the above embodiments, the complexation procedure further comprises drying the insoluble complex under vacuum and at a temperature ranging from 20° C. to 60° C.

In any or all of the above embodiments, the crystallization procedure comprises: exposing the insoluble complex of any of the above embodiments to a GRAS solvent and an acid to convert the insoluble complex to free cannabidiol; and treating the neutral species with water to provide crystals of substantially pure cannabidiol. In some embodiments, the crystallization procedure further comprises: forming a slurry comprising the neutral species and a GRAS solvent; and filtering and washing the slurry to provide crystals of substantially pure cannabidiol.

In some embodiments, a method is described comprising forming a (+)-menthadienol solution comprising (+)-menthadienol and heptane or an isomer thereof; forming a olivetol solution comprising olivetol and heptane or an isomer thereof; combining (+)-menthadienol solution and the olivetol solution with a Lewis Acid catalyst to form a first reaction mixture; exposing the first reaction mixture to a terpene-containing component to form a second reaction mixture; exposing the second reaction mixture to water to form an organic phase and an aqueous phase; separating the organic phase from the aqueous phase; exposing the organic phase to an aqueous alkaline solution; mixing the organic phase with the aqueous alkaline solution; filtering the organic phase to provide a clarified solution; mixing the clarified solution with an amine compound for a time sufficient to produce an insoluble complex; isolating the insoluble complex via filtration or centrifugation; washing the insoluble complex with a solvent; exposing the insoluble complex to a GRAS solvent and an acid to convert the insoluble complex to free cannabidiol; and (i) treating the free cannabidiol with water to provide crystals of substantially pure cannabidiol; or (ii) forming a slurry comprising the free cannabidiol and a GRAS solvent, and filtering and washing the slurry to provide crystals of substantially pure cannabidiol.

In some embodiments, a method is described comprising: forming a (+)-menthadienol solution comprising (+)-menthadienol and toluene; forming a olivetol solution comprising olivetol and toluene; combining (+)-menthadienol solution and the olivetol solution with a Lewis Acid catalyst to form a first reaction mixture; exposing the first reaction mixture to a terpene-containing component to form a second reaction mixture; exposing the second reaction mixture to water to form an organic phase and an aqueous phase; separating the organic phase from the aqueous phase; exposing the organic phase to an aqueous alkaline solution; mixing the organic phase with the aqueous alkaline solution; filtering the organic phase to provide a clarified solution; mixing the clarified solution with an amine compound for a time sufficient to produce an insoluble complex; isolating the insoluble complex via filtration or centrifugation; washing the insoluble complex with a solvent; exposing the insoluble complex to a GRAS solvent and an acid to convert the insoluble complex to free cannabidiol; and (i) treating the free cannabidiol with water to provide crystals of substantially pure cannabidiol; or (ii) forming a slurry comprising the free cannabidiol and a GRAS solvent, and filtering and washing the slurry to provide crystals of substantially pure cannabidiol.

Also disclosed herein is an insoluble complex, comprising cannabidiol and an amine selected from 1,4-diazabicyclo[2.2.2]octane, 1,3,7-trimethyl-3,7-dihydro-1H-purine-2,6-dione, nicotinamide, isonicotinamide, or 1,10-phenanthroline. In some embodiments, the cannabidiol and the amine are present in a 1:1 ratio.

In view of the many possible embodiments to which the principles of the present disclosure may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

We claim:

1. A method for making cannabidiol or a composition thereof, comprising:
    combining (+)-menthadienol and olivetol with a Lewis Acid catalyst to form a first reaction mixture;
    exposing the first reaction mixture to a terpene-containing component to form a second reaction mixture;
    exposing the second reaction mixture to water to form an organic phase and an aqueous phase;
    separating the organic phase from the aqueous phase; and
    contacting the organic phase with an amine compound for a time sufficient to produce an insoluble complex.

2. The method of claim 1, wherein the Lewis Acid catalyst is $Zn(OTf)_2$ or $Sc(OTf)_3$ and wherein the terpene-containing component is orange oil, orange terpenes, limonene, or a combination thereof.

3. The method of claim 1, wherein the (+)-menthadienol and olivetol are mixed together and then the Lewis Acid catalyst is added.

4. The method of claim 1, wherein the olivetol and the Lewis Acid catalyst are mixed together and then the (+)-menthadienol and is added.

5. The method of claim 1, wherein the olivetol, the (+)-menthadienol, or both are diluted with a diluting solvent prior to combining the olivetol and the (+)-menthadienol.

6. The method of claim 5, wherein the diluting solvent is an aliphatic solvent, an aromatic solvent, or a halogenated solvent.

7. The method of claim 1, further comprising performing an aqueous alkaline wash procedure prior to contacting the organic phase with the amine compound, comprising exposing the organic phase to an aqueous alkaline solution, mixing the organic phase with the aqueous alkaline solution, and filtering the organic phase; and/or isolating the insoluble complex via filtration or centrifugation and washing the insoluble complex with a solvent.

8. The method of claim 1, wherein the amine compound is 1,4-diazabicyclo[2.2.2]octane, 1,3,7-trimethyl-3,7-dihydro-1H-purine-2,6-dione, nicotinamide, isonicotinamide, or 1,10-phenanthroline.

9. The method of claim 1, wherein the insoluble complex comprises (i) cannabidiol and (ii) 1,4-diazabicyclo[2.2.2]octane, or 1,3,7-trimethyl-3,7-dihydro-1H-purine-2,6-dione, or nicotinamide, or isonicotinamide, or 1,10-phenanthroline.

10. The method of claim 1, further comprising drying the insoluble complex under vacuum and at a temperature ranging from 20° C. to 60° C.

11. The method of claim 1, further comprising exposing the insoluble complex to a Generally Recognized As Safe ("GRAS") solvent and an acid to convert the insoluble complex to free cannabidiol; and (i) treating the free cannabidiol with water to provide crystals of substantially pure cannabidiol; or (ii) forming a slurry comprising the free cannabidiol and a Generally Recognized As Safe ("GRAS") solvent, and filtering and washing the slurry to provide crystals of substantially pure cannabidiol.

12. A method for making cannabidiol or a composition thereof, comprising:
    forming a (+)-menthadienol solution comprising (i) (+)-menthadienol and (ii) toluene or heptane (or a heptane isomer);
    forming a olivetol solution comprising (i) olivetol and (ii) toluene or heptane (or a heptane isomer);
    combining (+)-menthadienol solution and the olivetol solution with a Lewis Acid catalyst to form a first reaction mixture;
    exposing the first reaction mixture to a terpene-containing component to form a second reaction mixture;
    exposing the second reaction mixture to water to form an organic phase and an aqueous phase;
    separating the organic phase from the aqueous phase;
    exposing the organic phase to an aqueous alkaline solution and mixing the organic phase with the aqueous alkaline solution;
    filtering the organic phase to provide a clarified solution; and
    mixing the clarified solution with an amine compound for a time sufficient to produce an insoluble complex.

13. The method of claim 12, further comprising isolating the insoluble complex via filtration or centrifugation.

14. The method of claim 13, further comprising exposing the insoluble complex to a Generally Recognized As Safe ("GRAS") solvent and an acid to convert the insoluble complex to free cannabidiol.

15. The method of claim 14, further comprising treating the free cannabidiol with water to provide crystals of substantially pure cannabidiol; or forming a slurry comprising the free cannabidiol and a Generally Recognized As Safe ("GRAS") solvent, and filtering and washing the slurry to provide crystals of substantially pure cannabidiol.

16. The method of claim 13, further comprising washing the insoluble complex with a solvent.

17. The method of claim 16, further comprising exposing the insoluble complex to a generally recognized as safe ("GRAS") solvent and an acid to convert the insoluble complex to free cannabidiol.

18. The method of claim 17, further comprising treating the free cannabidiol with water to provide crystals of substantially pure cannabidiol; or forming a slurry comprising the free cannabidiol and a generally recognized as safe ("GRAS") solvent, and filtering and washing the slurry to provide crystals of substantially pure cannabidiol.

19. The method of claim 6, wherein the aliphatic solvent is heptane, hexanes, pentane, cyclohexane, heptanes, hexane, or any and all combinations and/or isomers thereof; the aromatic solvent is benzene, toluene, ethylbenzene, xylenes, or any and all combinations thereof; and/or the halogenated solvent is 1,2-dichloroethane, dichloromethane, 1,2-dichloroethene, 1,1-dichloroethane, 1,1-dichloroethene, chlorobenzene, or any and all combinations thereof.

20. A method for making cannabidiol or a composition thereof, comprising:
    combining (+)-menthadienol and olivetol with a Lewis Acid catalyst to form a first reaction mixture;
    exposing the first reaction mixture to a terpene-containing component to form a second reaction mixture;
    exposing the second reaction mixture to water to form an organic phase and an aqueous phase;
    separating the organic phase from the aqueous phase;
    performing an aqueous alkaline wash procedure, comprising exposing the organic phase to an aqueous alkaline solution, mixing the organic phase with the aqueous alkaline solution, and filtering the organic phase to provide a clarified solution; and
    contacting the clarified solution with an amine compound for a time sufficient to produce an insoluble complex.

* * * * *